(12) United States Patent
Kato et al.

(10) Patent No.: US 6,867,322 B1
(45) Date of Patent: Mar. 15, 2005

(54) ESTER-FORMING MONOMER

(75) Inventors: Jinichiro Kato, Nobeoka (JP); Katsuhiro Fujimoto, Nobeoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/070,740

(22) PCT Filed: Sep. 13, 2000

(86) PCT No.: PCT/JP00/06289

§ 371 (c)(1),
(2), (4) Date: Mar. 12, 2002

(87) PCT Pub. No.: WO01/19764

PCT Pub. Date: Mar. 22, 2001

(30) Foreign Application Priority Data

Sep. 13, 1999 (JP) .......................................... 11/258509

(51) Int. Cl.[7] ........................ C07C 63/313; C07C 67/48; B32B 27/00; C08J 11/04; C08F 6/00
(52) U.S. Cl. ............................. 560/78; 521/40; 521/48; 521/48.5; 528/481; 528/492; 528/496; 528/503; 560/96; 562/480
(58) Field of Search .......................... 521/40, 48, 48.5; 528/481, 492, 496, 503; 562/480, 78, 96, 485; 428/411.1, 424; 560/78, 96

(56) References Cited

U.S. PATENT DOCUMENTS 2,884,443 A * 4/1959 Siggel et al. ................. 560/96
3,488,298 A * 1/1970 Barkery et al. .............. 562/485
3,776,945 A * 12/1973 Ligorati et al. ................ 560/96
5,532,404 A * 7/1996 Gallagher ..................... 560/78

FOREIGN PATENT DOCUMENTS

| EP | 0484963 | * 11/1991 |
| GB | 2041916 | * 9/1980 |
| JP | 50-82028 | 7/1975 |
| JP | 53-63338 | 6/1978 |
| JP | 06072922 | 3/1994 |
| JP | 06157402 | 6/1994 |
| JP | 09020703 | 1/1997 |
| WO | WO 94/18152 | 8/1994 |
| WO | WO 97/49652 | 12/1997 |

* cited by examiner

Primary Examiner—Cecilia J. Teang
Assistant Examiner—Taylor V. Oh
(74) Attorney, Agent, or Firm—Finnegan, Henderson, Farabow, Garrett, & Dunner, L.L.P.

(57) ABSTRACT

An ester-forming monomer obtained by depolymerization of polytrimethylene terephthalate and having an acrolein content of no greater than 0.5 wt %. Polymers obtained using the monomer and fibers, films and molded articles comprising the polymers. The ester-forming monomer is obtained by reacting polytrimethylene terephthalate with at least one compound selected from among monoalcohols, 1,3-propanediol and water in the presence of a basic substance. When the recovered ester-forming monomer is used as the starting material for production of a polymer, it is possible to produce a molding polymer for fibers, films and the like with quality equivalent to or higher than that obtained using virgin monomer.

8 Claims, No Drawings

ESTER-FORMING MONOMER

TECHNICAL FIELD

The present invention relates to an ester-forming monomer obtained by depolymerization of polytrimethylene terephthalate and to a process for its production, and more specifically it relates to a high-purity ester-forming monomer which can give a polymer with quality equivalent to or above that obtained using virgin monomer even when the recovered monomer is reused for polymer production, and to a process for its production.

BACKGROUND ART

Polytrimethylene terephthalate (hereunder abbreviated as "3GT") fibers have long been known as revolutionary fibers having properties similar to nylon fibers including a soft feel and excellent elastic recoverability due to a low elastic modulus, and easy dyeability, as well as properties similar to polyethylene terephthalate (hereunder abbreviated as "PET") fibers including wash-and-wear properties, dimensional stability and yellowing resistance. However, until very recently, no inexpensive production process for the starting material 1,3-propanediol had been established, and therefore industrial production of 3GT fibers has not been possible. An industrial production process for 1,3-propanediol was established in the late 1990s, leading to an immediate increase in 3GT fiber business.

From the standpoint of preservation of the environment and cost reduction, a new synthetic fiber business requires establishment of recycling techniques for the polymer waste, fiber waste or used fiber product waste created during the polymer or fiber production stages. In particular, it is essential to establish chemical recycling techniques whereby various types of recovered polymer waste are chemically decomposed for their recycling into useful raw materials.

For example, a chemical recycling technique for PET is disclosed in Japanese Unexamined Patent Publication HEI No. 6-72922 as a process whereby waste PET is hydrolyzed under hydrogen pressure in the presence of a hydrogenated catalyst to obtain terephthalic acid. Also, Japanese Unexamined Patent Publication SHO No. 53-63338 discloses a process whereby a polyester comprising an aromatic dicarboxylic acid and an aliphatic glycol having 2–6 carbon atoms is decomposed in the presence of a fatty acid such as acetic acid and an ester-exchange catalyst, and the aromatic dicarboxylic acid is recovered.

However, chemical recycling techniques for the 3GT fiber business has a very short history and has not yet been established.

3GT has a chemical structure similar to PET or polybutylene terephthalate, which may suggest that chemical recycling techniques for PET may be directly diverted. However, investigation by the present inventors has revealed that 3GT is much more susceptible to chemical and thermal degeneration than PET, and therefore when recovery techniques for PET are directly used, the recovery yield and quality of useful monomer is greatly reduced.

In WO97/49652 there is disclosed a process for monomer recovery from waste of polyester containing 2–70% of non-polymer components, and most of the description therein pertains to techniques for PET. Although this publication does describe the use of 3GT as an example of a polyester, the examples mention that methanol gas is blown into the 3GT at above 200° C. for a long period of 12 hours for depolymerization, and therefore when it is used for repolymerization the quality is greatly inferior to that of polymers obtained using virgin monomer.

Thus, since no chemical recycling technique has yet been established for 3GT, the expected future increase in 3GT business definitely implies the need for creation of such a technique.

DISCLOSURE OF THE INVENTION

It is an object of the present invention to establish a technique for recovering a high-purity ester-forming monomer from 3GT polymer at a high recovery yield. More specifically, its object is to provide an ester-forming monomer recovered at high purity, and a process for its production, whereby a polymer with quality equivalent to or above that obtained using virgin monomer can be provided even when the recovered monomer is reused for polymer production.

In order to solve the problems described above, the present inventors first investigated the reactions involved in the decomposition steps for 3GT.

The 1,3-propanediol produced upon decomposition of 3GT is characterized in that a portion thereof readily converts to acrolein or allyl alcohol during the recovery reaction represented by the following reaction formula:

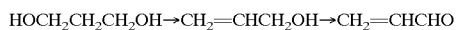

$$HOCH_2CH_2CH_2OH \rightarrow CH_2=CHCH_2OH \rightarrow CH_2=CHCHO$$

As a result of diligent research by the present inventors, it was found that when the production amount of acrolein or allyl alcohol increases, the yield of 1,3-propanediol is reduced and the purity of the recovered monomer is lowered, and that when monomer containing a large amount of acrolein is reused for production of 3GT, problems occur such as a slower polymerization reaction rate or coloration of the obtained polymer. In addition, it was further found that because of the high reactivity of acrolein, once it is generated it reacts with 1,3-propanediol as explained below, and the resulting reaction product causes further reaction leading to conversion to numerous different high boiling point substances. The present inventors have conjectured that the high reactivity of acrolein gives it a strong tendency to react with 1,3-propanediol, producing a compound with the 1,3-dioxane structure shown below having a chemically stable six-membered ring structure. This reaction product of acrolein, like acrolein itself, creates the same problem when 3GT is repolymerized.

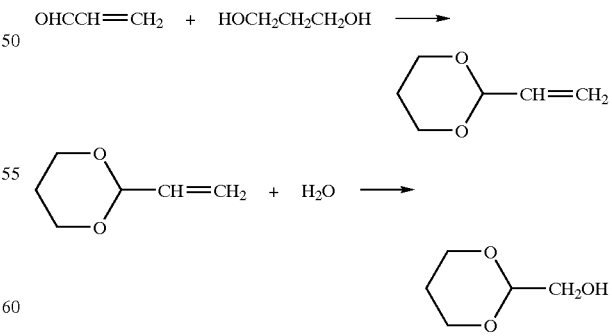

Because acrolein (boiling point: 53° C.) and allyl alcohol (boiling point: 97° C.) have much lower boiling points than 1,3-propanediol (boiling point: 214° C.), it might be assumed that they may be simply fractionated off even if produced in large quantities. Indeed, allyl alcohol has low reactivity and may therefore be separated from 1,3-propanediol relatively easily by distillation. In the case of acrolein, however, acrolein and 1,3-propanediol react to produce substances (an example of which is the compound shown above) with a boiling point close to that of 1,3-propanediol, making their separation very difficult to accomplish, and therefore a very serious impediment exists against high purification of 1,3-propanediol even by distillation. A similar problematic situation exists for distillation recovery of dialkyl terephthalates such as methyl terephthalate, in that acrolein degeneration products pose an impediment to separation. When obtaining terephthalic acid as well, acrolein or acrolein degeneration products are included in the terephthalic acid, and separation is difficult even using such separation means as recrystallization. Consequently, for recovery techniques it is a highly essential point to avoid generation of acrolein during the recovery process as much as possible.

On the other hand, the aforementioned problems do not occur in the case of PET which has a structure similar to 3GT. Ethylene glycol is in fact dehydrated during depolymerization of PET, producing acetaldehyde by way of keto-enol tautomerization. In the case of acetaldehyde, however, it further reacts with ethylene glycol producing a compound with an unstable 4-membered ring-containing oxetane structure, such that the aforementioned reaction in effect does not take place. Consequently, even though acetaldehyde is produced, it can be easily separated by distillation and the recovery reaction is greatly facilitated compared to 3GT.

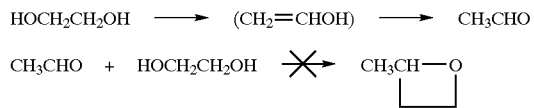

As explained above, a problem unique to 3GT has been faced when recovering monomer from 3GT waste, but at the current time the prior art offers no substantial recognition of the problem or proposal for its solution.

For example, although the above-mentioned publication WO97/49652 mentions the use of 3GT as an example of a polyester, absolutely no description is found recognizing the problem of acrolein generation, there is no mention of using a basic substance which decomposes acrolein as according to the present invention. Moreover, since the reaction temperature is high as mentioned above, the problem of generation of large amounts of acrolein is compounded by the considerably longer time required for depolymerization compared to the present invention, while high-temperature methanol gas is also necessary, which increases the energy and equipment cost and poses a problem in terms of safety in light of the risk of explosion of the high-temperature methanol gas, a flammable gas. Moreover, when waste 3GT is decomposed using the process of Japanese Unexamined Patent Publication HEI No. 6-72922 or Japanese Unexamined Patent Publication SHO No. 53-63338, acrolein or allyl alcohol are produced in large amounts, also posing the problem described above.

On the basis of this acquired knowledge, the present inventors examined in detail processes for decomposition of 3GT polymer waste to monomers, and as a result we have completed the present invention upon finding that in order to obtain a monomer with quality equivalent to or above that obtained using virgin monomer even when the recovered monomer is reused for polymer production, it is necessary to thoroughly eliminate the acrolein in the recovered monomer, and that in order to recover such a high purity monomer it is highly effective to employ a method wherein the acrolein is reacted with a basic substance to prevent the acrolein from being included in the recovered monomer.

In other words, the present invention relates a process for production of an ester-forming monomer characterized by being obtained by depolymerization of 3GT polymer and having an acrolein content of no greater than 0.5 wt %. The invention further relates to a process for production of an ester-forming monomer characterized by reacting 3GT polymer with at least one compound selected from a group consisting of monoalcohols, 1,3-propanediol and water in the presence of a basic substance. The invention still further relates to a process for production of an ester-forming monomer characterized by reacting 3GT polymer and 1,3-propanediol to first produce (3-hydroxypropyl) terephthalate and/or its oligomer, and then further reacting this with a monoalcohol in the presence of a basic substance.

The invention is directed to a polymer with an L value of 75 or greater and a b value of 10 or lower obtained using at least 1 wt % of the aforementioned ester-forming monomer, as well as fibers, films and molded articles composed of the polymer.

BEST MODE FOR CARRYING OUT THE INVENTION

The ester-forming monomer of the invention is obtained by depolymerization of 3GT and has an acrolein content of no greater than 0.5 wt %. Here, an "ester-forming monomer" is a monomer that can serve as a starting material for production of polyester, and generally is a diol, dicarboxylic acid ester or dicarboxylic acid. Specifically there may be mentioned 1,3-propanediol, monoesters of 1,3-propanediol, diesters of 1,3-propanediol, dialkyl terephthalates represented by dimethyl terephthalate and diethyl terephthalate, monoalkyl terephthalates represented by monomethyl terephthalate, bis(3-hydroxypropyl) terephthalate, methyl (3-hydroxypropyl) terephthalate, terephthalic acid, metal terephthalate salts, and the like. Particularly preferred among these ester-forming monomers are 1,3-propanediol, dimethyl terephthalate, bis(3-hydroxypropyl) terephthalate and terephthalic acid, because of their excellent reactivity as polyester starting materials.

The ester-forming monomer of the invention has an acrolein content of no greater than 0.5 wt % with respect to the amount of the recovered ester-forming monomer. When is an ester-forming monomer containing the residual acrolein reused as a polymerization starting material for 3GT, the polymerization rate is slowed and the whiteness of the obtained 3GT is reduced. A problem also occurs in that the acrolein further reacts, greatly hampering its separation from the recovered ester-forming monomer by distillation or the like. The acrolein content is preferably no greater than 0.1 wt %, and more preferably no greater than 0.05 wt %.

The recovered terephthalic acid, dimethyl terephthalate, bis(3-hydroxypropyl) terephthalate or 1,3-propanediol preferably has an acrolein content of no greater than 0.5 wt %, while a high transparency is preferred for improved whiteness of the 3GT obtained by repolymerization. When the ester-forming monomer is terephthalic acid, dimethyl terephthalate or bis(3-hydroxylpropyl) terephthalate, the b value is preferably 2 or lower, and more preferably 0.5 or lower. When the ester-forming monomer is 1,3-propanediol, the Hazen color is preferably 40 or below, more preferably 30 or below and most preferably 20 or below.

A preferred process for production of an ester-forming monomer according to the invention will now be explained.

The ester-forming monomer of the invention may be suitably produced by reacting the 3GT polymer with at least one compound selected from a group consisting of monoalcohols, 1,3-propanediol and water in the presence of a basic substance.

The 3GT polymer used for the invention may be 3GT waste in any form without restrictions, such as unused or used 3GT chip waste, extruder drain polymer, waste filaments yarn, waste film, waste resin products, used clothing, used industrial materials, used nonwoven fabrics, used carpets, etc. (hereunder also referred to as "3GT waste"). It may also be treated with an agent such as a dye, surface treatment agent or the like, and it may be in the form of an emulsion, suspension, solution or the like. The 3GT may be copolymerized, and for example, it may be copolymerized with 0.01–98 wt % of sodium-5-sulfoisophthalic acid, tetrabutylphosphonium 5-sulfoisophthalate, isophthalic acid, 1,4-butanediol, adipic acid, polyalkyleneglycol or the like. It may also include other polymers other than 3GT, for example, PET, polybutylene terephthalate, polyethylene naphthalate, polyethylene, polypropylene, polyacrylonitrile, polyamide, polycarbonate or the like, and it may even include waste other than polymers, such as metal waste, paper, inorganic matter, metals, food products and the like. In order to increase the 3GT monomer recovery yield, the 3GT content of the polymer is preferably 50 wt % or greater, more preferably 80 wt % or greater and most preferably 90 wt % or greater. The pre-recovery treatment preferably accomplishes removal of foreign matter such as metal, paper, stones, sand and the like, as well as appropriate washing for removal of substances included in the polymer such as additives, surface treatment agents, dyes and the like. The limiting viscosity (measurement method described below) of the 3GT used is not particularly restricted, but is preferably 0.2–2 from the standpoint of recovery efficiency.

According to the invention it is necessary to use at least one selected from a group consisting of monoalcohols, 1,3-propanediol and water for depolymerization of the 3GT polymer to the ester-forming monomer.

The depolymerization results in conversion to alkyl terephthalates such as dimethyl terephthalate or diethyl terephthalate and 1,3-dipropanediol when a monoalcohol is used, to bis(3-hydroxypropyl) terephthalate when 1,3-propanediol is used, and to terephthalic acid and/or its salts and 1,3-propanediol when water is used. A monoalcohol used for the invention is methanol, ethanol, propanol or the like. Methanol is particularly preferred since it can yield dimethyl terephthalate which can be purified by distillation. The amount of at least one selected from a group consisting of monoalcohols, 1,3-propanediol and water is not particularly restricted, but it is preferably 1–100 times and more preferably 1–10 times the weight of the 3GT polymer.

The basic substance to be used for the invention is an essential component for accelerating the reaction between the 3GT polymer and the monoalcohol, 1,3-propanediol and water, while also performing the role of reacting with the acrolein produced during the reaction process and converting the acrolein to non-volatile or non-soluble substances, or substances with very low volatility or solubility, thereby preventing inclusion of acrolein or acrolein degeneration products into the ester-forming monomer isolated by the procedures for isolation of the produced ester-forming monomer, such as the procedures of distillation, recrystallization, precipitation, etc. The basic substance also has the effect of increasing the recovery efficiency by inhibiting repolymerization by the catalyst added to the 3GT during isolation of the produced ester-forming monomer, for example, during the procedures of distillation, etc. If an acidic substance is used instead of a basic substance, the depolymerization reaction rate is notably lowered, while the acidic substance acts as a catalyst to accelerate dehydration reaction of the 1,3-propanediol, increasing the amount of acrolein or allyl alcohol produced and causing dimerization of the 1,3-propanediol, and thereby lowering the purity of the recovered monomer. The basic substance is not particularly restricted so long as it reacts with acids such as hydrochloric acid, sulfuric acid or acetic acid, and there may be mentioned salts that exhibit alkalinity when dissolved in water or alcohol and salts that do not dissolve in water or alcohol but can react with acids. Particularly preferred basic substances are basic metal salts that exhibit alkalinity when dissolved in water, from the standpoint of inhibiting by-products, and even more preferred are metal salts with a pH of 8–14 and more preferably 9–12. As specific basic substances there may be mentioned sodium carbonate, magnesium carbonate, potassium carbonate, barium carbonate, lithium carbonate, sodium hydroxide, potassium hydroxide, lithium hydroxide, magnesium hydroxide, melamine resins, polyurea, amino-substituted polystyrene, sodium acetate, sodium formate, potassium acetate, potassium formate and the like; with sodium carbonate and potassium carbonate being particularly preferred for obtaining 1,3-propanediol and dimethyl terephthalate, and sodium hydroxide and potassium hydroxide being preferred for obtaining 1,3-propanediol and terephthalic acid. The amount of the basic substance to be used is not particularly restricted, but is generally 0.01–200 mole percent and preferably 0.1–50 mole percent with respect to the total number of moles of the repeating unit of the 3GT (for example, 206 g of homo 3GT is considered as one mole).

There are no particular restrictions on the reaction temperature for the depolymerization, but it is preferably 50–450° C. At below 50° C., the reaction occurs only gradually and the recovery efficiency is poor. At above 450° C., by-products are produced resulting in considerable coloration of the recovered product. The temperature is more preferably 70–300° C. When the depolymerization temperature exceeds the boiling point of the solvent used, pressure may be applied to maintain a liquid state, in which case the solvent may be in a critical state. There are no particular restrictions on the reaction time, but because of the high efficiency of the process of the invention, the reaction may usually be completed within 10 hours, or even within 2 hours. In contrast, in the examples in WO97/49652 which specifically describe recovery of 3GT, a very long time of 12 hours is required for the depolymerization. It will therefore be appreciated that the process of the invention is an efficient, low-energy process.

More preferred production processes for different ester-forming monomers will now be explained.

For production of dialkyl terephthalates such as dimethyl terephthalate, or bis(3-hydroxypropyl) terephthalate, the 3GT polymer is preferably combined with a monoalcohol such as methanol or an alcohol such as 1,3-propanediol in the presence of a basic substance and hydrolysis is performed at a temperature of 50–450° C., from the standpoint of allowing a more rapid hydrolysis rate. A temperature of 50–300° C. is especially preferred. After the reaction, the solid phase and liquid phase are first separated, and in the case of a dialkyl terephthalate, separation may be accomplished by distillation. 1,3-dipropanediol may be isolated from the liquid phase by distillation. For the most preferred isolation method, the basic substance which is used is left completely or partially non-neutralized before separation of the solid phase and liquid phase. That is, it is particularly preferred for the isolation to be in a state in which the basic function of all or a portion of the basic substance is maintained. This is because complete neutralization prevents reaction between the acrolein and the basic substance, such that the acrolein or its degeneration products become included as impurities during the separation and separation is thus hampered. In addition, when an acid is used in excess for neutralization, the problem of dimerization of 1,3-propanediol tends to occur readily. In order to obtain a dialkyl terephthalate such as dimethyl terephthalate or diethyl terephthalate, the 3GT polymer may be reacted with 1,3-propanediol to first produce bis(3-hydroxypropyl) terephthalate and/or its oligomer, and then if necessary the bis(3-hydroxypropyl) terephthalate and/or its oligomer isolated and finally a monoalcohol such as methanol or ethanol allowed to act thereon in the presence of a basic substance. This method is in fact preferred for a higher recovery yield.

For production of terephthalic acid and 1,3-propanediol, it is preferred to combine the 3GT polymer with water in the presence of a basic substance and perform hydrolysis at pH 8–14 and a temperature of 150–450° C., for a higher hydrolysis rate. Hydrolysis produces terephthalic acid salts and 1,3-propanediol in the polyester component. In order to isolate each of the components, first the solid phase and liquid phase may be separated, a stronger acid than terephthalic acid such as sulfuric acid or phosphoric acid added to the solid phase to produce terephthalic acid, and a known solid/liquid separation method such as centrifugal separation or filtration applied for recovery. Separately, the liquid phase may be directly distilled to isolate 1,3-propanediol. The most preferred isolation method in this case as well involves no neutralization of the basic substance which is used before separation from the solid phase. Although neutralization with an acid is essential in order to obtain terephthalic acid, it is preferred from the standpoint of purity to accomplish the neutralization at 100° C. or below and preferably 50° C. or below, after separation of the 1,3-propanediol.

The ester-forming monomer obtained in the manner mentioned above may be reused as the starting material for an ester-based polymer such as 3GT, PET, polybutylene terephthalate or the like. The polymerization process in this case may be a publicly known process. The ester-forming monomer of the invention may, of course, be used as a mixture with a virgin monomer, in which case it may be used in an amount of 1 wt % or greater, preferably 10 wt % or greater and more preferably 70 wt % or greater of the monomer reused for polymerization.

Because of the high purity of the ester-forming monomer of the invention, a polymer which is reobtained therewith also has high quality. In particular, a whiteness equivalent to or superior to using a virgin monomer can be obtained, and a brightness-indicating L value of 75 or greater, preferably 80 or greater and more preferably 85 or greater can be achieved. In addition, a yellowing-indicating b value of 10 or below, preferably 7 or below and more preferably 5 or below can also be achieved. The polymer obtained in this manner is easy to work and allows production of high-quality fibers, films and molded articles.

EXAMPLES

The present invention will now be explained in further detail by way of the following examples.
(1) Acrolein Content The acrolein content was measured based on the $^1$H-NMR spectrum (nuclear magnetic resonance spectrum) of the recovered ester-forming monomer, or by gas chromatography.

(2) L Value, b Value

These were measured using a color computer by Suga Shikenki Co., Ltd.
(3) Hazen Color The sample was placed in a color comparison tube, the color was compared with standard color comparison tubes from Hazen Color No.10 to No.500, and the numerical value matching the sample and the standard color comparison tube was recorded as the Hazen color. In the case of no match, the nearest darker and lighter Hazen colors were determined and the median value was taken as the Hazen color.
(4) Recovery Yield The recovery yield was determined according to the following formula.

$$\text{Recovery yield} = A/B \times 100(\%)$$

A: Amount of ester-forming monomer actually recovered
B: Theoretical amount of ester-forming monomer recoverable by depolymerization of used polymer
(5) Limiting Viscosity The limiting viscosity [η] is the value determined based on the following formula definition.

$$[\eta] = \lim(\eta r - 1)/C$$

$C \to 0$

The symbol ηr in this formula is the value of the viscosity at 35° C. for a diluted solution of 3GT polymer dissolved in a 98% purity o-chlorophenol, divided by the viscosity of the solvent itself measured at the same temperature, and it is generally defined as the relative viscosity. The symbol C is the value of the solute weight in grams per 100 ml of the solution.

Example 1

After charging 144 g of 3GT chips with a limiting viscosity of 0.92, 255 g (3.36 moles) of 1,3-propanediol and 144 mg of sodium acetate (0.1 wt %/polymer, indicating units of wt % with respect to the polymer weight) in a 1 L autoclave, reaction was conducted at 210° C. for 60 minutes. After the reaction, the 1,3-propanediol was distilled off under reduced pressure at 0.4 mmHg. The obtained white solid was analyzed by $^1$H-NMR (measuring apparatus: 400 MHz FT-NMR Model DPX-400 by Bruker Co., Ltd.) and confirmed to be bis(3-hydroxypropyl) terephthalate. The conversion rate was approximately 100%.

With 130 g of the obtained bis(3-hydroxypropyl) terephthalate there were charged 224 g (7 moles) of methanol and 25.2 g (0.24 mole) of sodium carbonate in a 1 L autoclave, and the mixture was heated at 65° C. for 30 minutes. The pH during the decomposition reaction was 12. After the reaction, the product was adequately cooled and a centrifugal separator was used at 1500 rpm to separate the liquid phase (composed mainly of methanol and 1,3-propanediol, and also containing sodium acetate and sodium carbonate) and solid phase (composed mainly of dimethyl terephthalate and also containing sodium acetate and sodium carbonate). After completely distilling off the methanol in the liquid phase using an evaporator, the 1,3-propanediol was isolated by distillation under reduced pressure. Satisfactory results were obtained, with a recovery yield of 87%, an acrolein content of 0.02 wt %, and a Hazen color of 5. The dimethyl terephthalate in the solid phase was also isolated by distillation under reduced pressure. The results were satisfactory with an acrolein content of substantially 0 wt % in the recovered dimethyl terephthalate, a b value of 0.2 and no coloration.

Example 2

After charging 100 g of drain matter (drain waste) from extrusion of 3GT chips with a limiting viscosity of 0.9 and a moisture content of 30 ppm at 270° C., and 500 g of a 2 wt % aqueous sodium hydroxide solution in a 3 liter autoclave, hydrolysis was performed at 250° C. for 2 hours. The pH during the decomposition reaction was 13.5. No particular odor was found when the cover of the autoclave was opened.

After the reaction, the solid and liquid phases were separated and the solid phase was neutralized with dilute sulfuric acid at 0° C. to recover the terephthalic acid. The recovery yield was 80%. The acrolein content was less than 0.01 wt %, and the b value was 0.1. The liquid phase was not neutralized, and the 1,3-propanediol was isolated by distillation. The results were satisfactory with a recovery yield of 87%, an acrolein content of 0.02 wt % and a Hazen color of 5.

Comparative Example 1

Example 1 was carried out with addition of 5 drops of sulfuric acid instead of sodium carbonate. The pH during the decomposition reaction was 4. The recovery yield was very low at 35%.

Comparative Example 2

Example 2 was carried out using 2 N sulfuric acid for hydrolysis instead of the 2 wt % aqueous sodium hydroxide solution. The pH during the decomposition reaction was 1.3. An intense acrolein odor was noted when the autoclave cover was opened after the reaction. Terephthalic acid was also deposited. The produced terephthalic acid was isolated by filtration, but the recovery yield was low at 48%, the acrolein content of the terephthalic acid was 3.3 wt %, the b value was 3.9, and a yellowish tint was exhibited. The residual liquid was subjected to simple distillation under reduced pressure of 0.5 Torr to recover the 1,3-propanediol, but the recovery yield was low at 73%, the acrolein content was 4.5 wt %, the Hazen color was 50, and considerable coloration was exhibited.

Comparative Example 3

After charging 90 g of 3 GT chips with a limiting viscosity of 0.9, 10 g of PET chips with a limiting viscosity of 0.62, 1000 g of 1,3-propanediol and 15 g of 2 N sulfuric acid in a 3 L autoclave, the mixture was heated at 200° C. for 120 minutes. The pH during the decomposition reaction was 1.5. After the reaction, the product was cooled and a centrifugal separator was used at 1500 rpm to recover the bis(3-hydroxypropyl) terephthalate at a recovery yield of 47%. The acrolein content of the recovered bis(3-hydroxypropyl) terephthalate was 4.7 wt %, the b value was 4.6, and a yellowish tint was exhibited. The residual liquid was subjected to simple distillation under reduced pressure of 0.5 Torr to recover the 1,3-propanediol, but the recovery yield was low at 46%, the acrolein content was 4.2 wt %, the Hazen color was 45, and considerable coloration was exhibited.

Example 3

After charging 90 g of 3 GT chips with a limiting viscosity of 0.62, 2000 g of methanol and 90 mg of sodium carbonate in a 3 liter autoclave, the mixture was heated at 250° C. for 360 minutes. Here, the methanol was in a supercritical state. The pH during the decomposition reaction was 7.8.

After the reaction, the product was cooled and a centrifugal separator was used at 1500 rpm to recover the dimethyl terephthalate at a recovery yield of 90%. The acrolein content of the recovered dimethyl terephthalate was 0.03 wt %, and the b value was satisfactory at 0.26.

Upon distillation of the obtained dimethyl terephthalate under reduced pressure, the acrolein content of the recovered dimethyl terephthalate was 0 wt %, the b value was 0.1, and virtually no coloration was exhibited.

Example 4

After charging 194 g of commercially available dimethyl terephthalate, 160 g of the 1,3-propanediol recovered in Example 1 and 97 mg of calcium acetate in a polymerization boiler, the mixture was subjected to heating at 243° C. for 7 hours for ester-exchange reaction. After then adding 97 mg of titanium tetrabutoxide and 80 mg of trimethyl phosphate, heating was carried out at 270° C. for 3 hours under a vacuum of 0.1 Torr for polycondensation reaction. The limiting viscosity of the obtained 3GT was 0.85. The L value was 88 and the b value was satisfactory at 2.1.

In contrast, when the same amounts of commercially available dimethyl terephthalate as above and commercially available 1,3-propanediol (acrolein content: 0.01 wt %) were used for the same polymerization experiment as above, the L value of the obtained 3GT was 85, the b value was 8, and the whiteness of the 3GT obtained using the monomer recovered in Example 1 was superior.

After drying the repolymerized 3GT obtained in Example 4, it was extruded at 275° C. and then stretched to an elongation of 40% to make 55 dtex/24 f fibers. The strength of the fibers was 3.7 cN/dtex, the elastic modulus was 22 cN/dtex, and the recoverability after 20% extension was 85%. A filament thereof was used to make a tube-shaped netting. The netting was soft and had an excellent stretch property. For comparison, fibers were obtained by spinning the aforementioned 3GT with a b value of 14. The fiber properties were approximately equivalent to those of the 3GT fibers obtained using the recovered monomer, with a strength of 3.5 cN/dtex, an elongation of 41% and a recoverability after 20% extension 83%.

Example 5

The 3GT with a b value of 8 polymerized using commercially available 1,3-propanediol in Example 4 was depolymerized by the same method as Example 1. The acrolein content of the 1,3-propanediol obtained by the depolymerization was 0.02 wt %, and the Hazen color was satisfactory at 5. The acrolein content of the recovered dimethyl terephthalate was substantially 0 wt %, and the b value was satisfactory at 0.2. When the recovered monomer was used for repolymerization of 3GT by the method of Example 4, the L value was 88, the b value was 2.3, and virtually no coloration was exhibited.

Example 6

After drying the repolymerized 3GT obtained in Example 4, it was extruded from a T-die at 275° C. and rapidly cooled with a cooling roll to obtain an undrawn film. The undrawn film was preheated at 85° C., and then a tenter was used for stretching the undrawn film at a draw ratio of 3.3 in the longitudinal direction at 78° C. and then at a draw ratio of 3.5 in the lateral direction at 77° C. The elastic modulus of the obtained film was 3 GPa in both the longitudinal and lateral directions, indicating a tough film. A film was also fabricated in the same manner using the 3GT with a b value of 8 mentioned in Example 4. The properties were not different from those of the film obtained using the 3GT of Example 4, but a slight degree of yellow coloration was exhibited.

Example 7

After drying the repolymerized 3GT obtained in Example 4, it was extruded through a die at 275° C. to fabricate a dumbbell-shaped molded article. The tensile strength was 150 MPa and the impact strength was 95 J/m. For comparison, a dumbbell was also fabricated in the same manner using the 3GT with a b value of 8 mentioned in Example 4. It had a tensile strength of 148 MPa and an impact strength of 94 J/m, and exhibited yellow coloration.

INDUSTRIAL APPLICABILITY

According to the present invention, it is possible to recover high-purity starting monomer at high efficiency from 3GT-containing fibers, films, resin articles and waste polymer discharged in production stages. In particular, it is possible to obtain 3GT without coloration by repolymerization using recovered monomer according to the invention after a first polymerization, even from commercially available 1,3-propanediol with reduced coloration by an effect due to impurities. While the reason is not clearly understood, it is conjectured that the problematic impurities are probably removed during the depolymerization step. By employing the process of the invention it is possible to obtain monomer of higher quality than the virgin monomer and to utilize the starting material without waste, and the invention therefore represents a highly useful technology from the standpoint of environmental preservation and manufacturing cost reduction.

When ester-forming monomer recovered according to the invention is reused as a starting material for production of 3GT or even polymers other than 3GT, such as PET, it is possible to obtain polymers with quality equivalent to or higher than that obtained using virgin monomer. The resulting polymers are useful for fibers, films and molded articles. The recovered ester-forming monomer is also useful as an intermediate starting material for various types of chemical and medical products.

What is claimed is:

1. A process for producing an ester-forming monomer by the depolymerization of poly(trimethylene terephthalate) comprising:

reacting a poly(trimethylene terephthalate) with 1,3-propanediol to obtain bis (3-hydroxypropyl) terephthalate and/or an oligomer thereof;

reacting the bis (3-hydroxypropyl) terephthalate and/or an oligomer thereof with methanol in the presence of a basic metallic salt capable of exhibiting an alkaline pH of from 8 to 14 when dissolved in water and at a temperature of 50 to 450° C. to produce an ester-forming monomer; and isolating the ester-forming monomer while keeping the basic metallic salt in complete or partial non-neutralization.

2. The process for producing an ester-forming monomer according to claim 1, wherein the ester-forming monomer is 1,3-propanediol.

3. The process for producing an ester-forming monomer according to claim 1, wherein the ester-forming monomer is dimethyl terephthalate.

4. An ester-forming monomer produced by the process according to claim 2, wherein the 1,3-propanediol contains acrolein in an amount not greater than 0.5 wt % and has a Hazen Color No. of 40 or less.

5. An ester-forming monomer produced by the process according to claim 3, wherein the dimethyl terephthalate contains acrolein in an amount not greater than 0.5 wt % and has a yellow-indicating b value of 2 or less.

6. A poly(trimethylene terephthalate) polymer obtained by a polymerization of a 1,3-propanediol component containing at least 1 wt % of the 1,3-propanediol according to claim 4, wherein the polymer has a brightness-indicating L value of 75 or more and a yellow-indicating b value of 10 or less.

7. A polymer (trimethylene terephthalate) polymer obtained by a polymerization of a dimethyl terephthalate component containing at least 1 wt % of the dimethyl terephthalate according to claim 5, wherein the polymer has a brightness-indicating L value of 75 or more and a yellow-indicating b value of 10 or less.

8. A poly(trimethylene terephthalate) polyester shaped article in the form of film or fiber, wherein the shaped article is formed of the polymer according to claim 6 or 7.

* * * * *